United States Patent [19]

Porro

[11] Patent Number: 5,589,459

[45] Date of Patent: Dec. 31, 1996

[54] SYNTHETIC PEPTIDES FOR DETOXIFICATION OF BACTERIAL ENDOTOXINS AND FOR THE PREVENTION AND TREATMENT OF SEPTIC SHOCK

[75] Inventor: Massimo Porro, Siena, Italy

[73] Assignee: BiosYnth s.r.l., Siena, Italy

[21] Appl. No.: 280,397

[22] Filed: Jul. 26, 1994

Related U.S. Application Data

[60] Division of Ser. No. 819,893, Jan. 16, 1992, Pat. No. 5,371,186, which is a continuation-in-part of Ser. No. 658,744, Feb. 11, 1991, abandoned.

[51] Int. Cl.$^6$ .................... A61K 38/00; A61K 38/12; C07K 5/00; C07K 7/00
[52] U.S. Cl. .................... 514/15; 514/9; 514/11; 514/16; 514/17; 514/18; 530/317; 530/330; 530/327; 530/328; 530/329
[58] Field of Search .................... 514/9, 11, 15, 514/16, 17, 18, 885, 921; 530/317, 330, 327, 328, 329; 424/2, 9; 422/405, 28; 210/764; 252/106, 89.1

[56] References Cited

U.S. PATENT DOCUMENTS 5,358,933 10/1994 Porro .................... 514/15
5,371,186 12/1994 Porro .................... 530/328

FOREIGN PATENT DOCUMENTS 9314115 7/1993 WIPO.

OTHER PUBLICATIONS

Shieh et al., *FEBS Lett.*, vol. 252, No. 1, 2, pp. 121–124, Jul. 1989.

Danner et al., *Antimicrobial Agents and Chemotherapy*, vol. 33, No. 9, pp. 1428–1434, Sep. 1989.

*Primary Examiner*—Avis M. Davenport
*Attorney, Agent, or Firm*—Hedman, Gibson & Costigan, P.C.

[57] ABSTRACT

The present invention provides methods of using peptides of the formula $R_1$—(A—B—C)$_n$—R, wherein $R_1$ and R are independently H or an amino acid residue or a fatty acid residue; A is an amino acid residue selected from the group consisting of Lys and Arg; B is an amino acid selected from the group consisting of Phe, Tyr, and Trp; C is an amino acid selected from the group consisting of Leu, Ile and Val; n is an integer of 1–100. The peptides are used for the removal of endotoxin from blood or sera; the detoxification of bacterial endotoxin; and the prevention of the contamination of products with endotoxin.

14 Claims, 1 Drawing Sheet

FIG. 1

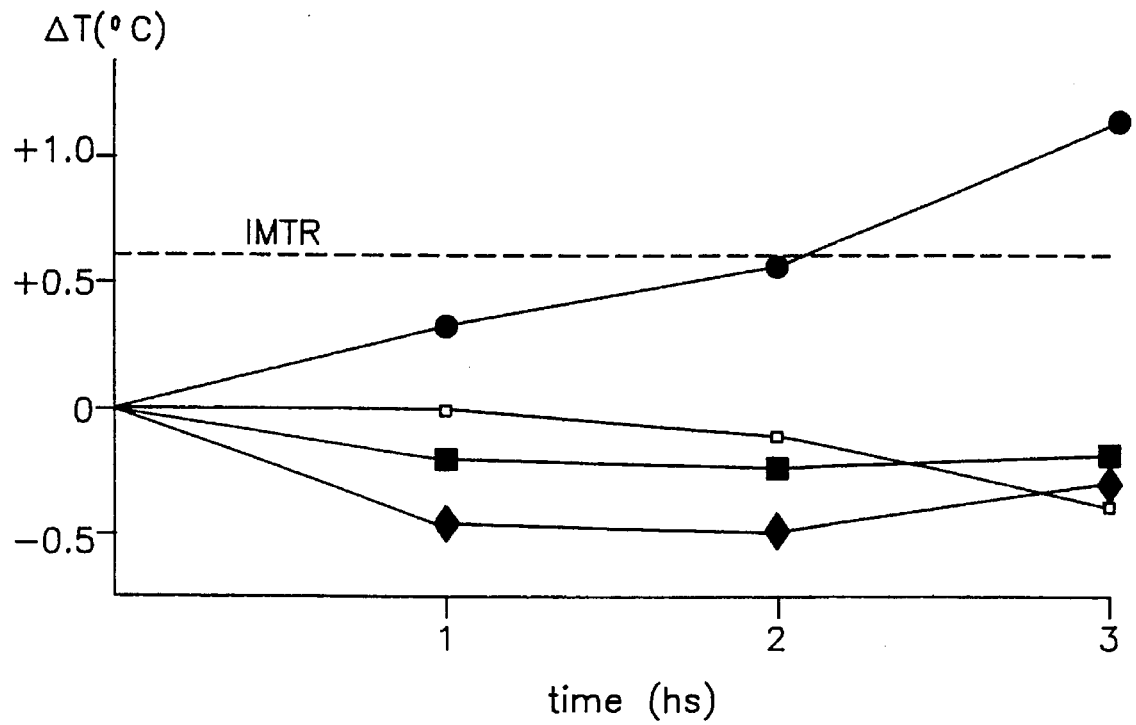

The value 0 corresponds to the mean of the control temperature (T=39.54±0.05°C), for the twelve rabbits tested.

● positive control: endotoxin 30 ng/Kg body weight

□ negative control: endotoxin 30 ng/Kg body weight complexed with 60 ng Polymyxin "B"

■ endotoxin 30 ng/Kg body weight complexed with 60 ng Peptide II.

◆ endotoxin 30 ng/Kg body weight complexed with 300 ng Peptide I.

IMTR: Individual Maximal Temperature Rise allowed by the U.S. Pharmacopeia (vol. XXI), The National Formulary (vol. XVI), Combined Edition, January, 1985.

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) TOPOLOGY: circular ( i i ) SEQUENCE DESCRIPTION: SEQ ID NO:1:

Cys  Lys  Phe  Leu  Lys  Lys  Cys
        1                          5

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) TOPOLOGY: circular ( i i ) SEQUENCE DESCRIPTION: SEQ ID NO:2:

Lys  Thr  Lys  Cys  Lys  Phe  Leu  Lys  Lys  Cys
        1                        5                        10

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) TOPOLOGY: circular ( i i ) SEQUENCE DESCRIPTION: SEQ ID NO:3:

Lys  Phe  Leu  Lys  Lys  Thr
        1                        5

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( C ) TOPOLOGY: circular ( i i ) SEQUENCE DESCRIPTION: SEQ ID NO:4:

Cys  Lys  Lys  Leu  Phe  Lys  Cys  Lys  Thr  Lys
        1                        5                        10

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) TOPOLOGY: circular ( i i ) SEQUENCE DESCRIPTION: SEQ ID NO:5:

Cys  Lys  Lys  Leu  Phe  Lys  Cys  Lys  Thr
        1                        5

( 2 ) INFORMATION FOR SEQ ID NO:6:

( i ) SEQUENCE CHARACTERISTICS:
        ( A ) LENGTH: 11 amino acids
        ( B ) TYPE: amino acid
        ( C ) TOPOLOGY: circular ( i i ) SEQUENCE DESCRIPTION: SEQ ID NO:6:

```
Ile Lys Thr Lys Cys Lys Phe Leu Lys Lys Cys
 1               5                   10
```

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( C ) TOPOLOGY: linear ( i i ) SEQUENCE DESCRIPTION: SEQ ID NO:7:

```
Ile Lys Thr Lys Lys Phe Leu Lys Lys Thr
 1               5                   10
```

( 2 ) INFORMATION FOR SEQ ID NO:8:

( i ) SEQUENCE CHARACTERISTICS:
        ( A ) LENGTH: 11 amino acids
        ( B ) TYPE: amino acid
        ( C ) TOPOLOGY: circular ( i i ) SEQUENCE DESCRIPTION: SEQ ID NO:8:

```
Ile Lys Phe Leu Lys Phe Leu Lys Phe Leu Lys
 1               5                   10
```

( 2 ) INFORMATION FOR SEQ ID NO:9:

( i ) SEQUENCE CHARACTERISTICS:
        ( A ) LENGTH: 7 amino acids
        ( B ) TYPE: amino acid
        ( C ) TOPOLOGY: linear ( i i ) SEQUENCE DESCRIPTION: SEQ ID NO:9:

```
Lys Phe Leu Lys Phe Leu Lys
 1               5
```

( 2 ) INFORMATION FOR SEQ ID NO:10:

( i ) SEQUENCE CHARACTERISTICS:
        ( A ) LENGTH: 9 amino acids
        ( B ) TYPE: amino acids
        ( C ) TOPOLOGY: linear ( i i ) SEQUENCE DESCRIPTION: SEQ ID NO:10:

```
Arg Tyr Val Arg Tyr Val Arg Tyr Val
 1               5
```

SYNTHETIC PEPTIDES FOR DETOXIFICATION OF BACTERIAL ENDOTOXINS AND FOR THE PREVENTION AND TREATMENT OF SEPTIC SHOCK

This is a divisional of application Ser. No. 07/819,893, filed Jan. 16, 1992 now U.S. Pat. No. 5,371,186, which is a continuation-in-part of Ser. No. 07/658,744, filed Feb. 11, 1991 and now abandoned.

BACKGROUND OF THE INVENTION

Shock, which is induced by endotoxin, is known as septic shock (SS). This condition is a life-threatening situation which occurs following infections by Gram-negative bacteria as complication of surgery, prolonged hospitalization, accidents and other traumatic events. It is today well recognized that the agent responsible for this disease is the bacterial endotoxin, a glycolipid antigen present only on the surface of Gram-negative bacteria. This glycolipid is also known as lipo-poly saccharide (LPS) or lipo-oligosaccharide (LOS) depending from the size of the carbohydrate chain which is covalently bound to the fatty-acid-rich moiety called Lipid A (LipA). Only Lipid A is responsible of the major toxic effects shown by endotoxin (LPS). Once endotoxin is released in the blood-stream by bacteria, specialized cells of the immune system like macrophages and monocytes are activated by the endotoxin and several immune mediators are released (Cytokines such as Interleukin-1 and Interleukin-6; α—Tumor necrosis factor; γ—Interferon). Furthermore, endotoxin also activates the complement cascade which results in cell lysis with the consequent release of proteolytic enzymes promoting the release of vasoactive effectors from platelets (e.g.: bradykinine and histamine). The final result is death of the patient in 40–60% of the cases within 48–72 hours. So far, there has been no specific cure or therapy available although bolus injections of adrenal corticosteroids such as methylprednisolone are used.

Polymyxin "B" is known as a molecule that binds and detoxifies bacterial endotoxins and can prevent septic shock when given therapeutically in animal models. However, Polymyxin "B" is a toxic product in vitro and in vivo and this fact limits its potential as a therapeutic agent for the treatment of septic shock.

Septic shock can be caused by infection with any bacteria that cause the release of LPS. These bacteria include *Pseudomonas aeroqinosa, Escherichia coli, Salmonella typhi, Neisseria meningitidis, Neisseria gonorrheae, Bordetella pertussis, Klebsiella pneumoniae* and the like.

The reasons leading to the reported toxicity of Polymyxin B are not completely understood but they are most likely related to the peculiarity of its amino acid composition, specifically for the content of Lα—γ—, diamino butyric acid (DAB) (49.1% w/w of the structure) which is an analog of the aa Lysine (reported in literature as able to substitute Lysine in the protein synthesis) and for the presence of D-Phenylalanine an isomer of the naturally occurring L-Phenylalanine. Other possible reasons, still related to the aa composition, could be related to the high stability of Polymyxin "B" to proteolytic enzymes as well as to the possible binding to cell receptors structurally comparable to the Lipid A moiety of LPS (the gangliosides of the nervous tissues are glycolipids with N,O—acyl ($C_{14}$–$C_{18}$) chains closely related to the N,O—acyl chains present in the Lipid A structure).

The applicants have discovered new conformational peptides that are structurally different from Polymyxin (in virtue of their amino acid composition) but are capable of binding to the same binding site within Lipid A of endotoxins (LOS and LPS) that Polymyxin "B" will also bind. The relative binding efficiency of the new peptides is comparable to the affinity constant value of Polymyxin "B". The complex formed when Lipid A or LPS are reacted with the peptides of the invention is non-toxic and the natural antigenicity of Lipid A and LPS is maintained.

As a consequence of this high-affinity binding to the Lipid A moiety of endotoxins, most of the synthetic peptide analogs have shown the ability to detoxify endotoxins as evidenced by in vitro as well as in vivo analysis. The in vitro test used, as measure of detoxification, the inhibition of the enzymatic cascade leading to the coagulation of the Lymulus lysate (LAL test) by endotoxin. The LAL test is recognized as the most sensitive and predictive test for the toxic and pyrogenic activity of LPS, since pyrogenicity in vivo is related to the release of the endogenous immune modulators Interleukin-1 (IL-1) and alfa-Tumor necrosis factor (α-TNF), the mediators responsible for the fatalities associated to septic shock. As an in vivo test confirming detoxification of LPS, was then used the Rabbit pyrogen test performed according to the United States Pharmacopeia XXI.

This discovery thus provides a new class of compounds that may be used in the treatment of septic shock. It is anticipated that the new peptides will not exhibit in humans the toxic effects of Polymyxin "B", in virtue of their completely natural amino acid composition as well as for their limited resistance to proteolytic degradation in human serum.

Accordingly, it is a primary object of the invention to provide novel prophylactic and therapeutic agents which may be used in the treatment of septic shock.

It is also an object of this invention to provide novel peptide compounds which may be used in the treatment of septic shock.

It is also an object of this invention to provide novel pharmaceutical compositions which may be used in the treatment of septic shock.

It is also an object of this invention to provide novel complexes of Lipid-A or LPS and a peptide which are antigenic and non-toxic.

It is also an object of this invention to provide a method of producing novel non-toxic Lipid A or LPS antigens.

Conditions other than septic shock where an endotoxin is produced may also be treated by the peptides of the invention using the same dose of peptides which is used to treat septic shock. These conditions include pertussis bacterial meningitis and viral HIV-related infections.

These and other objects of the invention will become apparent from a review of the present specification.

BRIEF DESCRIPTION OF THE DRAWINGS

FIG. 1 is a graph that shows the effect of peptides of the present invention on endotoxin.

DETAILED DESCRIPTION OF THE INVENTION

The invention provides novel monomeric, linear polymeric, cyclic monomeric or cyclic polymeric peptides of the formula having amphipathic-polycationic characteristics of the formula:

$$R_1-(A-B-C)_n-R \qquad (I)$$

wherein $R_1$ and R are independently H or an amino acid residue or a fatty acid residue; A is an amino acid residue selected from the group consisting of Lys, Arg and His; B is an amino acid selected from the group consisting of Phe, Tyr and Trp; C is an amino acid selected from the group consisting of Leu, Ile and Val; n is an integer of from 1–100, and preferably 1–10. These peptides are useful in the treatment of septic shock.

A preferred formula according to formula I is formula II:

$$R^1—(Lys\text{-}Phe\text{-}Leu)_n—R \quad\quad (II)$$

wherein n is an integer of from 1–100 preferably 1–10 and R and $R^1$ are H or may be any of the naturally occurring amino acids or fatty acids with an alkyl chain length encompassing between 1 and 20 (or more) methylene groups; those peptides which have the retro-oriented aa sequences of the described peptides; those peptides which have the enantiomer aa sequences or diastereomer aa sequences of the described peptides; and those peptides which have the aa shifted in place with regard to their original positions which provide a peptide which is useful in the treatment of septic shock.

Examples of peptides of formulas I and II include:

| Group I | Group II |
|---|---|
| (Lys—Phe—Leu)$_n$ | (Arg—Phe—Leu)$_n$ |
| (Lys—Phe—Val)$_n$ | (Arg—Phe—Val)$_n$ |
| (Lys—Phe—Ile)$_n$ | (Arg—Phe—Ile)$_n$ |
| (Lys—Tyr—Leu)$_n$ | (Arg—Tyr—Leu)$_n$ |
| (Lys—Tyr—Val)$_n$ | (Arg—Tyr—Val)$_n$ |
| (Lys—Tyr—Ile)$_n$ | (Arg—Tyr—Ile)$_n$ |
| (Lys—Trp—Leu)$_n$ | (Arg—Trp—Leu)$_n$ |
| (Lys—Trp—Val)$_n$ | (Arg—Trp—Val)$_n$ |
| (Lys—Trp—Ile)$_n$ | (Arg—Trp—Ile)$_n$ |

Specific examples of these peptides include:

Cys—Lys—Phe—Leu—Lys—Lys—Cys
S —— —— —— —— —— —— S   (SEQ ID NO: 1)

Lys—Thr—Lys—Cys—Lys—Phe—Leu—Lys—Lys—Cys   (SEQ ID NO: 2)
S —— —— —— —— —— —— S   (SEQ ID NO: 3)

Lys—Phe—Leu—Lys—Lys—Thr   (SEQ ID NO: 4)

Ile—Lys—Thr—Lys—Lys—Phe—Leu—Lys—Lys—Thr

Cys—Lys—Lys—Leu—Phe—Lys—Cys—Lys—Thr—Lys
S —— —— —— —— —— —— S   SEQ ID NO: 5

Cys—Lys—Lys—Leu—Phe—Lys—Cys—Lys—Thr
S —— —— —— —— —— —— S   SEQ ID NO: 6

Ile—Lys—Thr—Lys—Cys—Lys—Phe—Leu—Lys—Lys—Cys
                S —— —— —— —— —— —— S   SEQ ID NO: 7

Ile—Lys—Phe—Leu—Lys—Phe—Leu—Lys—Lys—Phe—Leu—Lys   SEQ ID NO: 8

Lys—Phe—Leu—Lys—Phe—Leu—Lys   SEQ ID NO: 9

Arg—Tyr—Val—Arg—Tyr—Val—Arg—Tyr—Val   SEQ ID NO: 10

The novel peptides are useful for the prophylaxis or treatment of septic shock in mammals including humans at doses of about 0.1 µg–2.0 mg/kg of body weight or may be used at a level of about 10 µg to about 0.1 mg/kg of body weight and the amount may be administered in divided doses on daily basis. The peptides may be administered prophylactically to patients who may be exposed to or have been exposed to organisms which may cause septic shock or to detoxify bacterial endotoxins by the use of the same dose set forth above in vivo. In vitro detoxification or prevention of endotoxin contamination may be carried out at a level of which is effective to achieve the desired result. The amount may be based on routine experimentation based on the premise about 1 mole of endotoxin is bound by 1 mole of peptide as shown in Table III. The particular dose of a particular peptide may be varied within or without the range that is specified herein depending on the particular application or severity of a disease and the condition of the host. Those who are skilled in the art may ascertain the proper dose using standard procedures.

The compounds may be administered intravenously and parenterally using well known pharmaceutical carriers or inert diluents. Oral administration is not preferred because the peptides will tend to be degraded by the enzymes of the alimentary tract. Water or isotonic saline are preferred diluents and a concentration of 0.1 mg per ml may be used. Preferably, the compounds will be stored in a dry form and will be dissolved in the diluent immediately prior to administration.

The novel peptides may be synthesized by classical methods of peptide chemistry using manual or automated techniques as well as by DNA recombinant technology. The synthetic procedure comprises solid phase synthesis by Fmoc chemistry, cleavage (TFA 95%+Et—(SH)$_2$ 5%), followed by vacuum evaporation. Thereafter, the product is dissolved in 10% acetic acid, extracted with ether, concentrated at 0.1 mg/ml at pH of 6.0–7.5. Stirring under filtered air followed for 1 to 6 hours in case of the Cysteine-containing peptides and finally desalting by reverse phase chromatography is carried out.

Generally, the complexes of Lipid-A and LPS with the peptides of the invention may be made using stoichiometric amounts of Lipid-A or LPS with the peptide. The amounts of complex also able to induce antibody in a host are not critical; about 1 mcg of Lipid-A in the complex with the peptide has been shown to be effective in safely inducing antibodies in a host.

The activity of the peptides has been confirmed by the direct microprecipitin assay with *B. pertussis* Lipid A, and *B. pertussis* LPS. In addition, the binding activity for LPS as compared to Polymyxin "B" has been demonstrated on the basis of the ratio of peptide/LPS and peptide/Lipid A on a w/w basis. The data from the Limulus (LAL) test shows that the novel compounds, when tested at a proper concentration, have equivalent LAL inhibition to Polymyxin "B".

The invention also includes the use of the peptide to contact systems containing endotoxin dispersed in a fluid for the purpose of detoxifying the endotoxin. This procedure may be used to detoxify biopharmaceuticals such as vaccines, solutions of drugs, injectable nutrient solutions, and the like. The invention further comprises the use of the peptides as additives for fluids which will support bacterial growth that will produce endotoxin. The presence of the non-toxic peptide will detoxify any endotoxin which is subsequently elaborated.

The peptides of the invention have not been shown to exhibit in vitro the peculiar antibiotic activity of polymyxin B against clinically relevant bacteria such as *Vibrio cholerae*, *Salmonella Typhi* and *Haemophilus influenzae* at concentrations as high as 1 mg/ml. The novel peptides disclosed herein have not shown hemolytic activity on human red blood cells ex vivo at concentrations of as high as 1 mg/ml.

The peptides have not exhibited acute toxicity in vivo when injected in Swiss Webster mice at 50 mg/kg after 48 hours observation and beyond. The $LD_{50}$ for polymyxin B is 2.5–5 mg/kg for the same species of mice.

No abnormal toxicity has been shown in mice or guinea pigs following i.p. injection according to the US CFR Title 21 610.11(b). The test animals were observed for seven days or beyond and did not exhibit any signs of abnormality.

In addition, the novel compounds have been shown to be relatively unstable in the presence of proteolytic enzymes such as trypsin while it has been confirmed that Polymyxin "B" is stable in the presence of trypsin. These results show that the novel compounds are useful for the treatment of septic shock.

DESCRIPTION OF THE PREFERRED EMBODIMENTS

The following exemplifies the preferred procedure for the synthesis of the compounds of the invention.

Using the following procedure, peptides have been synthesized using the automatic synthesizer MILLIGEN Mod. 9050 (MILLIPORE, Burlington, Mass.) on a solid phase support of polyamide/Kieselguhr resin (2.0 g). The amino acids used in the synthesis of the peptide analogs were Fmoc-aa-Opfp derivatives (9-Fluorenylmethyloxycarbonyl-aa-O-pentafluorophenyl ester) of each amino acid (aa) involved in the considered sequences using 0.8 mmol of each amino acid to sequentially form the peptide.

Each cycle of synthesis was performed at r.t. (20° C.) and involved the following steps of reaction:
Step 1—Deprotection The first aa Fmoc-protected at the amino group, was treated with a 20% solution of piperidine for 7 minutes in order to remove the Fmocα-protecting group. Washing with dimethylformamide followed for 12 minutes to remove all traces of piperidine. Deprotection and washing were run continuously through the column containing the resin by mean of pump at a flow of 5 ml/min.
Step 2—Activation of the Fmoc-aa-Opfp derivative
The amino and carboxy-protected amino acid due, according to the desired sequence, was activated after its dissolution in 5 ml of dimethylformamide, by catalytic amount of hydroxybenzotriazol (0.5 ml of a 5% w/v solution in dimethylformamide).
Step 3—Acylation
The activated and protected Fmoc-aa-Opfp derivative was then recycled for 30 minutes through the column by the pump at 5 ml/min in order to obtain coupling of the introduced aa at the α-amino group (previously deprotected as reported in Step 1) of the amino acid preceding the new one in the desired sequence.
Step 4—Washing
Washing of the matrix in the column followed by dimethylformamide for 2 minutes at 5 ml/min before a new cycle began.

At the completion of the synthesis, the peptide on the resin support was cleaved by 95% Trifluoroacetic acid (TFA) with 5% Ethane dithiol as scavenger, if Cysteine residues were present in the aa sequence, at room temperature for 2 hours. After separation of the cleaved peptide from the resin by filtration, the solution was concentrated by vacuum evaporation to dryness. The collected solid residue was then solubilized in 10% acetic acid at a concentration of 10–20 mg/ml and several extractions by diethyl ether followed (six to eight extractions with half of the volume of the peptide solution) in order to remove the scavenger Ethane dithiol. The peptide solution was then neutralized by 0.1N ammonium hydroxide and adjusted to the concentration of roughly 0.1 mg/ml. The solution was then stirred under air for 1 to 6 hours. in order to obtain the selective oxidation of the two sulphydryl groups belonging to the Cys residues of the sequence. In this way, only monomeric oxidized peptides were obtained with no traces of polymeric material. The solution of oxidized peptide was then desalted by reverse-phase chromatography on SEP-PAK C-18 cartridges (MILLIPORE) and finally freeze-dried. The products were analyzed by high-performance liquid chromatography (HPLC) analysis as well as by chemical analysis of the synthetic structures.

Fast Atom Bombardment Mass Spectrometry was used to confirm the calculated mass of the peptides.

The following peptides were prepared using the procedure which has been set forth above:

```
Cys—Lys—Phe—Leu—Lys—Lys—Cys                             I
S — — — — — — — — — — — S   SEQ ID NO: 1

Lys—Thr—Lys—Cys—Lys—Phe—Leu—Lys—Lys—Cys                 II
            S — — — — — — — — — — — S   SEQ ID NO: 2

Lys—Phe—Leu—Lys—Lys—Thr SEQ ID NO: 3                    III

Cys—Lys—Lys—Leu—Phe—Lys—Cys—Lys—Thr—Lys                 IV
S — — — — — — — — — S   SEQ ID NO: 4

Cys—Lys—Lys—Leu—Phe—Lys—Cys—Lys—Thr                     V
S — — — — — — — — S   SEQ ID NO: 5

Ile—Lys—Thr—Lys—Cys—Lys—Phe—Leu—Lys—Lys—Cys             VI
                S — — — — — — — — — — — S   SEQ ID NO: 6

Ile—Lys—Thr—Lys—Lys—Phe—Leu—Lys—Lys—Thr   SEQ ID NO: 7  VII

Ile—Lys—Phe—Leu—Lys—Phe—Leu—Lys—Phe—Leu—Lys  SEQ ID NO: 8   VIII
```

Lys—Phe—Leu—Lys—Phe—Leu—Lys    SEQ ID NO: 9    IX

Arg—Tyr—Val—Arg—Tyr—Val—Arg—Tyr—Val    SEQ ID NO: 10    X

The amino acid composition of each peptide was determined by PICO-TAG after acid hydrolysis by 6N hydrochloric acid for 1–12 hours at 150° C. and was found to be as follows:

TABLE I

| PEPTIDE | AMINO ACID | AMINO ACID COMPOSITION[1] (moles aa/mol peptide) | |
|---|---|---|---|
| | | EXPECTED | FOUND |
| I | Cys | 2.00 | 2.13 |
| | Leu | 1.00 | 1.06 |
| | Lys | 3.00 | 2.90 |
| | Phe | 1.00 | 1.01 |
| II | Cys | 2.00 | 2.16 |
| | Leu | 1.00 | 0.99 |
| | Lys | 5.00 | 4.95 |
| | Phe | 1.00 | 0.96 |
| | Thr | 1.00 | 1.03 |
| III | Leu | 1.00 | 0.98 |
| | Lys | 3.00 | 2.99 |
| | Phe | 1.00 | 1.01 |
| | Thr | 1.00 | 1.05 |
| IV | Cys | 2.00 | 2.15 |
| | Leu | 1.00 | 0.94 |
| | Lys | 5.00 | 4.97 |
| | Phe | 1.00 | 0.93 |
| | Thr | 1.00 | 1.10 |
| V | Cys | — | 1.85 |
| | Leu | — | 0.94 |
| | Lys | — | 4.04 |
| | Phe | — | 0.98 |
| | Thr | — | 1.06 |
| VI | Cys | 2.00 | 2.14 |
| | Ile | 1.00 | 0.98 |
| | Leu | 1.00 | 0.99 |
| | Lys | 5.00 | 4.98 |
| | Phe | 1.00 | 0.94 |
| | Thr | 1.00 | 1.00 |
| VII | Ile | 1.00 | 0.98 |
| | Leu | 1.00 | 1.00 |
| | Lys | 5.00 | 4.99 |
| | Phe | 1.00 | 0.98 |
| | Thr | 2.00 | 2.00 |
| VIII | Ile | 1.00 | 0.98 |
| | Leu | 3.00 | 2.98 |
| | Lys | 4.00 | 3.92 |
| | Phe | 3.00 | 3.02 |
| IX | Leu | 2.00 | 1.90 |
| | Lys | 3.00 | 3.10 |
| | Phe | 2.00 | 1.90 |
| X** | Arg | 3.00 | 3.00 |
| | Tyr | 3.00 | 2.95 |
| | Val | 3.00 | 2.90 |

*V is generated by tryptic hydrolysis in human serum from the synthetic analog IV.
**Peptide X was cleaved from the resin overnight at r.t. by 95% trichloroacetic acid containing 5% phenol as a scavenger.

All peptides of the above reported formulas were compared with Polymyxin "B" in a direct microprecipitin assay for Lipid A and LPS of B. Pertussis (5 μg each) in order to detect their precipitating (binding) activity:

TABLE II

| ppt | μg | nmol | Complex |
|---|---|---|---|
| Polymyxin "B" | 7.3 | 6.1 | +++ |
| Peptide I | 5.3 | 6.1 | ++ |

TABLE II-continued

| ppt | μg | nmol | Complex |
|---|---|---|---|
| Peptide II | 7.5 | 6.1 | +++ |
| Peptide III | 4.7 | 6.1 | +— |
| Peptide IV | 7.5 | 6.1 | +++ |
| Peptide V | 7.5 | 6.1 | +++ |
| Peptide VI | 8.2 | 6.1 | +++ |
| Peptide VII | 7.5 | 6.1 | +++ |
| Peptide VIII | 8.7 | 6.1 | +++ |

Quantitation of the amount of precipitated peptides present in the complexes with LPS of B. pertussis has been done by amino acid analysis after acid hydrolysis (by 6 M HCl) of the complexes recovered by centrifugation at 3,000 rpm×15 minutes. In Table III, the stoichiometry of some complexes is reported as calculated by the ratio (on molar basis) between the amount of each peptide and the amount of Lipid A present in the structure of LPS used in the experiments:

TABLE III

STOICHIOMETRY OF THE COMPLEXES FORMED BETWEEN $LPS_{bp}$* AND SYNTHETIC PEPTIDE ANALOGS OF POLYMYXIN "B"

| | Amount of peptide** in the complex (nmoles) | Ratio peptide/LipA (mol/mol) |
|---|---|---|
| Polymyxin "B" | 2.69 | 1.02 |
| Peptide II | 3.39 | 1.28 |
| Peptide IV | 3.55 | 1.34 |
| Peptide VI | 3.12 | 1.18 |
| Peptide VII | 3.00 | 1.13 |
| Peptide VIII | 3.86 | 1.46 |

*Complexes formed between 10 μg of B. Pertussis LPS (equivalent to 4.50 μg of Lipid A or 2.64 nmoles) and 10 μg of peptide (twice the amount corresponding to the saturation point found for Polymyxin "B" in the analysis of AFFINITY)
**Values represent the average of two separate experiments of amino acid analysis after acid hydrolysis of the recovered complexes.

To further characterize the binding activity of the synthetic peptides for Lipid A of endotoxin, experiments of direct competition with Polymyxin "B" have been set-up in order to evaluate the Affinity constant value of Polymyxin "B" for the toxic moiety of endotoxin and ultimately to calculate the Selectivity of the synthetic peptide analogs (ratio on molar basis, between the affinity constant value of a given peptide and that of Polymyxin "B" for Lipid A). Table IV shows the relative values of Affinity and those of Selectivity for the investigated peptides:

TABLE IV

CHARACTERISTICS OF THE COMPLEXES FORMED BETWEEN $LPS_{bp}$ AND SYNTHETIC PEPTIDE ANALOGS OF POLYMYXIN "B"

| Peptide | AFFINITY (Ka) (L/Moles) | SELECTIVITY ($Ka_{ANA}/Ka_{PCP}$) | AMOUNT OF ppt* |
|---|---|---|---|
| Polymyxin "B" | $1.15 \times 10^7$ | 1.0 | +++ |
| Peptide I | $<1.15 \times 10^5$ | <0.01 | +— |

TABLE IV-continued

CHARACTERISTICS OF THE COMPLEXES FORMED BETWEEN $LPS_{bp}$ AND SYNTHETIC PEPTIDE ANALOGS OF POLYMYXIN "B"

| Peptide | AFFINITY (Ka) (L/Moles) | SELECTIVITY ($Ka_{ANA}/Ka_{PCP}$) | AMOUNT OF ppt* |
|---|---|---|---|
| Peptide II | $0.56 \times 10^7$ | 0.49 | +++ |
| Peptide VI | $0.29 \times 10^7$ | 0.25 | +++ |
| Peptide IV | $0.49 \times 10^7$ | 0.43 | +++ |
| Peptide VII | $0.19 \times 10^7$ | 0.17 | +++ |
| Peptide VIII | $1.29 \times 10^7$ | 1.12 | +++ |
| Peptide IX | $0.1 \times 10^7$ | 0.10 | +++ |
| Peptide X | $0.27 \times 10^7$ | 0.24 | +++ |

*Detected as amount of precipitate obtained by microprecipitation in capillary tubes and by immunodiffusion in agarose.

The results obtained by the Limulus (LAL) test, shown in Table V, support the data obtained by measuring the Affinity of the peptides of the invention for the Lipid A moiety of LPS in that they were substantially equivalent to Polymyxin "B" in the inhibition of LPS activity on Limulus. The only peptide that showed a lower activity in the LAL inhibition was Peptide I which gave the lowest affinity constant value among the peptides reported in the present invention. Peptide I was, in fact, the one presenting the non complete structure needed for the mimick of Polymyxin "B" as the synthetic peptide analogs II, IV, VI and VII have clearly shown in the previous Table IV. It is important to note that the LAL test is accepted by the most important institutions in the Public Health field (World Health Organization, United States Food and Drug Administration, etc.) as a predictive test for absence of pyrogenicity in injectable material and it can be used to replace the in vivo test of pyrogenicity in rabbits.

TABLE V

INHIBITION OF LPS-INDUCED GELATION IN LAL TEST* BY SYNTHETIC PEPTIDES MIMICKING THE STRUCTURE OF POLYMYXIN "B"

| | LPS/Pept (w/w) | TEST** |
|---|---|---|
| LPS (0.1 μg LPS) | | POSITIVE |
| Polymyxin "B" (0.1 μg + LPS (0.1 μg) | 1 | NEGATIVE |
| Peptide I (0.1 μg) + LPS (0.1 μg) | 1 | POSITIVE |
| Peptide I (1.0 μg) + LPS (0.1 μg) | 10 | NEGATIVE |
| Peptide I (10.0 25 g) + LPS (0.1 μg) | 100 | NEGATIVE |
| Peptide II (0.1 μg) + LPS (0.1 μg) | 1 | NEGATIVE |
| Peptide III (100 μg) + LPS (0.1 μg) | 1000 | POSITIVE |
| Peptide IV (0.1 μg) + LPS (0.1 μg) | 1 | NEGATIVE |
| Peptide VI (0.1 μg) + LPS (0.1 μg) | 2 | NEGATIVE |
| Peptide VII (0.1 μg) + LPS (0.1 μg) | 2 | NEGATIVE |
| Peptide IX | 100 | NEGATIVE |
| Peptide X | 20 | NEGATIVE |

*The test had a sensitivity of 0.125 Endotoxin Units/ml equivalent in our case (LPS of B. Pertussis) to 0.4 ng/ml of LPS. The complexes were allowed to form at 37° C. for 30 minutes before to be processed for analysis after dilution 1/100 with saline.
**Values are representative of a minimum of three different analysis.

The results indicate that in order to mimick the structure of Polymyxin "B" for efficiently binding and detoxifying LPS, a synthetic peptide needs to have almost the complete aa sequence of Polymyxin "B" (Peptides II, IV, VI and VII contain ten and eleven aa residues versus ten aa residues of Polymyxin "B") with analogous (but not identical) chemical features. In contrast Peptide III, which contains only six aa residues (the linear sequence of the peptide-cycle in Polymyxin "B") is not able to efficiently bind and detoxify LPS. The minimal structure able to detoxify LPS appears to be Peptide I (corresponding to the peptide-cycle of Polymyxin "B") which, however, does not show an Affinity value comparable to the other peptide analogs showing a longer aa sequence.

The effects of trypsin present in human serum on Polymyxin "B" and the peptides of the invention was determined by combining 10 μl of human serum with 20 μg of the given peptide in 10 μl volume and holding the mixture at a temperature of 37° C. for different intervals of time. At various times, an aliquot of the mixture was processed by HPLC analysis in order to detect the residual amount of the investigated peptide. In Table VI the half-lives time of each peptide investigated are shown as compared to the half-life time of Polymyxin "B".

TABLE VI

STABILITY OF SYNTHETIC PEPTIDE ANALOGS OF POLYMYXIN "B" TOWARDS PROTEOLYSIS BY TRYPSIN IN HUMAN SERUM

| Peptide (%) | Half-Life Time (t/2) (min) | AMOUNT RECOVERED (%) after 180 mins |
|---|---|---|
| Polymyxin "B" | >>180 | 100 |
| Peptide I | >180 | 70 |
| Peptide II | 50 | 10 |
| Peptide VI* | 1,080 (18 hours) | 76 |
| Peptide IV** | 18 | 0 |
| Peptide V | 240 | 55 |
| Peptide VII | 50 | 28 |
| Peptide VIII | 7 | 0 |
| Peptide IX | 10 | 0 |
| Peptide X | 35 | 0 |

*Tryptic hydrolysis of Peptide VI generates Peptide II
**Tryptic hydrolysis of Peptide IV generates Peptide V As already mentioned in the background of the invention, the pyrogenic activity of LPS in vivo is due to the release from macrophages and monocytes of the cytokines Interleukin-1 (IL-1) and α-Tumor Necrosis Factor (α-TNF) the leading molecules responsible for the fatal effects of septic shock.

In order to verify "in vivo" the detoxifying activity of the peptides, we have injected five groups of three rabbits each with the complexes formed by two representative synthetic peptide analogs with LPS. The pyrogenicity test has been executed according to the United States Pharmacopeia (Vol. XXI)/The National formulary (Vol. XVI), Combined Edition, Jan. 1, 1985. As a negative control in the test, the complex formed by Polymyxin "B" and LPS was injected. As a positive control free LPS was injected. The results are reported in the FIG. 1. As one can see, LPS has shown its peculiar pyrogenic activity starting the first hour from the injection and the temperature continued to increase until the third hour of observation as required by the test. The peculiar behavior of a febrile pattern induced by LPS, involves two waves of temperature increase (biphasic behavior): The first temperature increase (first wave) it is shown within two hours from the injection of LPS and it is due to the immediate impact of the antigen on the host's immune system. The second and more consistent temperature increase (second wave) appears in the third hour from the injection of LPS and it is mediated by the endogenous pyrogens IL-1 and α-TNF released from the immune competent cells stimulated by LPS. The two complexes formed with LPS by the Peptide I and Peptide II as well as by Polymyxin "B" did not show either of the two waves of temperature increase, demonstrating that the two immune mediators IL-1 and α-TNF were not released in vivo upon injection of (complexed) pyrogenic doses of LPS. The results are shown in FIG. 1.

The following experiments compared the antibiotic activity of Polymyxin "B" with various peptides of the invention.

The tests were performed on BHI plates with liquid cultures of the test organism to give a lawn. Each peptide was diluted in water and placed on sterile Wathmam 3M disks on the surface of the plate. The plates were dried and incubated at 37° C. The zone of inhibition was measured after 18 hours:

bacteria was demonstrated by the LAL test. The results are shown in Table VII:

| SOURCE OF ENDOTOXIN | EU/ml IN REACTION | PEPTIDE/LPS (w/w) | TEST* | EFFICIENCY** OF BINDING (%) |
|---|---|---|---|---|
| B. Pertussis | 4 | 1 | Negative | >98 |
| E. Coli 055:B5 | 4 | 1 | Negative | >98 |
| P. Aeruginosa | 4 | 1 | Negative | >98 |
| S. Typhosa | 4 | 1 | Negative | >98 |
| K. Pneumoniae | 4 | 1 | Negative | >98 |
| S. Minnesota | 4 | 1 | Negative | >98 |
| S. Marcescens | 4 | 1 | Negative | >98 |
| S. Flexneri | 4 | 1 | Negative | >98 |
| E. Coli 0111:B4 | 4 | 1 | Negative | >98 |
| V. Cholerae | 4 | 1 | Negative | >98 |

*Average of three replicative analysis
**Efficiency of binding >98% corresponds to <0.08 Eu/ml of free endotoxin (NEGATIVE LAL TEST). Efficiency of binding of only 97% corresponds to 0.12 EU/ml of free endotoxin (POSITIVE LAL TEST).

| Compound | Concentration mg/ml | Zone (mm) of inhibition | | |
|---|---|---|---|---|
| | | S. typhi | H. influenzae | V. cholerae |
| Polymyxin "B" | 1.0 | 4 | 6 | 5 |
| | 0.2 | 2 | 3 | 2.5 |
| | 0.04 | 1 | 0 | 2 |
| | 0.008 | 0 | 0 | 1 |
| Peptide I | 1.0 | 0 | 0 | 0 |
| | 0.2 | 0 | 0 | 0 |
| | 0.04 | 0 | 0 | 0 |
| | 0.008 | 0 | 0 | 0 |
| Peptide II | 1.0 | 0 | 0 | 0 |
| | 0.2 | 0 | 0 | 0 |
| | 0.04 | 0 | 0 | 0 |
| | 0.008 | 0 | 0 | 0 |
| Peptide VI | 1.0 | 0 | 0 | 0 |
| | 0.2 | 0 | 0 | 0 |
| | 0.04 | 0 | 0 | 0 |
| | 0.008 | 0 | 0 | 0 |

The effect of the peptides of the invention on LPS-induced polyclonal B-cell activation was demonstrated by culturing spleen cells from unimmunized healthy SJL/J mice with 50 µg/ml of LPS and Polymyxin "B" or the peptides of the invention at the indicated concentrations. Cells were cultured in RPMI medium containing 1.0% normal mouse serum at 37° C. for 3 days. Cultures were pulsed with 1.0 µi/well of 3 H-thymidine for 16 hours and harvested for counting on an LS betaplate counter. The results were as follows:

| Units (µg/ml) | 3H-thymidine incorporation (cpm) | | |
|---|---|---|---|
| | PmB | Peptide I | Peptide II |
| none | 22,737 | 22,737 | 22,737 |
| 100 | 4,128 | 3,287 | 2,266 |
| 50 | 2,831 | 2,775 | 2,355 |
| 25 | 3,559 | 2,582 | 2,445 |
| 12.5 | 2,366 | 2,385 | 2,350 | cpm measured with non stimulated cultures=2,449.

The binding efficiency of Peptide II to the endotoxin which is elaborated by clinically important gram negative bacteria was demonstrated by the LAL test.

Peptide VI of the invention was labeled with Biotin which acts as a sensitive marker to provide a bi-specific molecule able to selectively react with Lipid A of bacterial endotoxins through Peptide VI ($Ka=0.3\times10^7$) and with the high affinity natural protein Avidin through the labeling molecule Biotin ($Ka=10^{15}$). The combination of the two selective and high affinity reactions, allows detection of Lipid A of endotoxins at very low levels (picomolar level or $10^{-12}$ Moles/liter). The reaction of Biotin-Avidin is used as an example for detecting the reaction between Lipid A/LPS and one of the peptides of the invention.

Peptide VI was conjugated to N-hydroxysuccinimidyl Biotin (1:1 mol/mol) in 0.1M sodium acetate solution at pH=6.0. The reaction was kept at 37° C. for 1 hour. In these conditions only the -amino group of the amino terminal aa (Ile) reacts so that the resulting peptide is monosubstituted and does not lose affinity for Lipid A. The labeled peptide was purified by reverse-phase liquid chromatography (HPLC) and chemically analyzed for aa composition and free amino groups. Analysis confirmed that biotinilation of the peptide occurred at the ratio 1:1 mol/mol.

Affinity for Lipid A/LPS and half-life time in human serum or human whole blood of the labeled Peptide VI (when tested according to the methods described herein were found not significantly different from the values reported in the same application ($Ka=0.3\times10^7$ Moles/liter and t/2=20 hours, respectively).

Affinity of the peptide bound-Biotin for Avidin, was found not significantly different from the one detected for free Biotin. At equivalent concentrations (1 nmol/ml) free and peptide-bound Biotin competed similarly for Avidin, as estimated by inhibition of the reaction between peroxidase-labeled Biotin and Avidin in a solid-phase DOT-BLOT assay on nitrocellulose.

By virtue of the found stoichiometry of the complex peptide/Lipid A (1:1 mol/mol) and that one known for the complex Biotin/Avidin (4:1 mol/mol), it becomes possible to estimate an unknown amount of endotoxin in a given sample, by titration of the amount of the labeled peptide which is bound to endotoxin and which is revealed by the reaction between the labeling agent (i.e. Biotin) and its specific reagent (i.e. enzyme-labeled Avidin).

The results demonstrate the preparation of a novel high sensitive and selective reagent able to reveal even traces of endotoxin in fluids (i.e. serum, blood and acqueous solutions).

Lipid A and LPS derived from B. pertussis have been detoxified with the stoichiometric amount of Peptide II and injected in mice respectively at the dose of 1 and 2 μg with and without 1 mg/dose of the adjuvant aluminum hydroxide. The immunization schedule included three doses given subcutaneously, three weeks apart. At the end of the immunization period, sera of the 10 mice/group were pooled and analyzed for the presence of antibodies (IgG and IgM isotypes) specific for the Lipid A moiety of endotoxin, at each stage of the immunization period (week 0, 3, 6 and 8).

Titers were analyzed for specificity and quantitative amount of antibodies by solid phase assay (DOT-BLOT on nitrocellulose). Nitrocellulose sheets were coated with Lipid A or LPS at 10 or 20 μg/ml in PBS pH=7.2 for 7 hours at room temperature. After washing the nitrocellulose with PBS containing 3% BSA w/v, the sera pool of mice was incubated at various dilutions with the Lipid-A-coated nitrocellulose, overnight at room temperature. Then, the Peroxidase-labeled anti-IgG or anti-IgM antibody was added for 2 hours at room temperature, followed by repetitive washing and by the substrate 4-chloronaphthol at 0.3% w/v. The enzymatic reaction was developed for 0.5–1 hour at room temperature in the dark.

Results of the anti-IgG and anti-IgM titers in the sera pool of mice, are reported in Tables VIII and IX. They show that when Lipid A as well as LPS are injected in a mammalian host in the form of complexes, after detoxification by the peptides of the invention, their natural antigenic repertoire is still intact and a specific serologic response is generated by the host's immune system. No antibodies were induced that were specific for the peptide present in the complex injected. Animals did not show any sign of hemorrhagic lesions or skin necrosis at the sites of injection after each dose of the complexes.

Thus, the peptides of the invention provide a novel method for the modification of a toxic antigen like Lipid A or LPS which may be used in a mammalian host in the form of safe, non-toxic complexes expressing the natural and specific antigenic repertoire of the bacterial endotoxin to induce immunity to the mammalian host.

Antibodies may be recovered from the antiserum using conventional procedures such as ammonium sulfate or alcohol precipitation and affinity-chromatography, in order to use the isolated Lipid A/LPS-specific antibodies for diagnostic use in fluids as well as for treatment of septic shock in a host.

TABLE VIII

Anti-Lipid A IgG Response
(sera pool of mice treated with Lipid A
or LPS detoxified with Peptide II)

| Week | Dilution$^{-1}$ (with Al(OH)$_3$) | Dilution$^{-1}$ (without Al(OH)$_3$) |
|---|---|---|
| 0 | 0 | 0 |
| 3 | 50 | 50 |
| 6 | 100 | 50 |
| 8 | 200 | 100 |

TABLE IX

Anti-Lipid A IgM Response
(sera pool of mice treated with Lipid A or LPS
detoxified with Peptide II)

| Week | Dilution$^{-1}$ (with Al(OH)$_3$) | Dilution$^{-1}$ (without Al(OH)$_3$) |
|---|---|---|
| 0 | 0 | 0 |
| 3 | 50 | 25 |
| 6 | 200 | 50 |
| 8 | 100 | 50 |

Prevention of endotoxin-induced death in mice, has been achieved by intravenous injection of the peptides of the invention. For this experiment, a strain of mice highly sensitive to the lethal activity of bacterial endotoxin has been used. Mice sensitized with Actinomycin D (Strain CD1) show a high sensitivity to extremely low doses of endotoxin. A dose as low as 1 μg of endotoxin per mouse (about 40 μg/kg of body weight) is able to completely kill a population of mice within 24–48 hours.

Groups of 20 mice CD1 have been treated intravenously with the peptides of the invention, with a single dose of 0.1 mg peptide, solubilized in sterile saline, per mouse. Thirty minutes later, mice were challenged by intraperitoneal injection of 1 μg of endotoxin purified from E. Coli strain 055-B5. Surviving mice were recorded every 24 hours during a seven days—period of observation. Parallel experiments were performed using comparable doses of Polymyxin B (PmB) and Chlorpromazine (CPZ, an anti-histaminic drug recently shown to be highly effective in preventing lethality in this strain of mice by challenge of endotoxin), as positive controls. Negative controls received an intravenous injection of saline.

Table X shows the results obtained: the survival rate of the mice treated by the peptides of the invention followed a behavior predictable from the affinity constant value of the peptides for Lipid A (see Table IV).

TABLE X

| | SURVIVAL RATE IN CD1 MICE SENSITIZED WITH ACTINOMYCIN D | | | | | | | |
|---|---|---|---|---|---|---|---|---|
| | 24 | 48 | 72 | 96 | 120 | 144 | 168 hs. | Significance |
| NaCl | 5 (25%) | 3 (15%) | 1 (5%) | 1 (5%) | 1 (5%) | 1 (5%) | 1 (5%) | |
| Peptide I | 8 (40%) | 4 (20%) | 3 (15%) | 3 (15%) | 3 (15%) | 3 (15%) | 3 (15%) | $p < 0.02$ |
| Peptide II | 13 (65%) | 8 (40%) | 8 (40%) | 8 (40%) | 8 (40%) | 8 (40%) | 8 (40%) | $p < 0.001$ |
| Peptide | 5 | 5 | 5 | 5 | 5 | 5 | 5 | |

TABLE X-continued

SURVIVAL RATE IN CD1 MICE SENSITIZED WITH ACTINOMYCIN D

|     | 24    | 48    | 72    | 96    | 120   | 144   | 168 hs. | Significance |
|-----|-------|-------|-------|-------|-------|-------|---------|--------------|
| VI  | (25%) | (25%) | (25%) | (25%) | (25%) | (25%) | (25%)   | $p < 0.01$   |
| PMB | 10    | 8     | 6     | 6     | 6     | 6     | 6       |              |
|     | (50%) | (40%) | (30%) | (30%) | (30%) | (30%) | (30%)   | $p < 0.001$  |
| CPZ | 10    | 10    | 10    | 10    | 10    | 10    | 10      |              |
|     | (50%) | (50%) | (50%) | (50%) | (50%) | (50%) | (50%)   | $p < 0.001$  |

There were 20 mice per group. Mice surviving at each of the seven 24 hours observation periods are listed. The % survival appears in parenthesis. P expresses the level of statistical significance calculated by "t-Test" for each molecule compared to the treatment with saline, considering the total survival rate in each group.

Peptide II shows a higher efficacy in comparison to PmB ($p<0.05$).

Peptide II shows the same efficacy of CPZ ($p<0.2$).

Another experiment, performed in mice (Strain Balb/c) naturally resistent to high doses of endotoxin (up to 0.5 mg/mouse), gave further evidence of the safety and efficacy of the peptides of the invention with respect to a comparable treatment performed with Polymyxin B.

Groups of 20 mice Balb/c have been treated intravenously with the peptides of the invention at the dose of 1 mg/mouse or with 0.1 mg/mouse of Polymyxin B (the highest dose of this drug tolerated in the mouse, when injected alone). Thirty minutes later, mice were challenged by intraperitoneal injection of 1 mg endotoxin from E.C strain 055-B5. Surviving mice were recorded every 24 hours during a seven days—period of observation. Negative controls received an intravenous injection of saline.

Table XI shows the results obtained: treatment of the animals by the peptides of the invention, resulted safe and efficacious. By contrast, treatment with Polymyxin B resulted efficacious only within three days following the endotoxin challenge, since immediately thereafter the toxicity of Polymyxin B (PmB) played a synergistic role with endotoxin and all mice died.

COMPARATIVE EXAMPLE

In further support of the features described for the peptide of claim I, and required for the binding activity to Lipid A, a peptide of the formula:

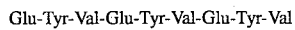

Glu-Tyr-Val-Glu-Tyr-Val-Glu-Tyr-Val analog of the Peptide X but showing poly-anionicity rather than poly-cationicity (Arg residues replaced by Glutamic acid residues) was synthesized and showed neither binding activity for Lipid A/LPS nor inhibition of the toxic activity of LPS in the LAL assay.

The peptides of the invention may be used in conjunction with Polymyxin-B at level which is in a stoichiometric excess of the Polymyxin-B calculated on the basis of the selectivity shown in Table IV in order to reduce the toxicity of Polymyxin B.

TABLE XI

SURVIVAL RATE IN BALB/c MICE

|         | 24     | 48    | 72    | 96    | 120   | 144   | 168 hs. | Significance |
|---------|--------|-------|-------|-------|-------|-------|---------|--------------|
| NaCl    | 12     | 10    | 8     | 8     | 8     | 8     | 8       |              |
|         | (60%)  | (50%) | (40%) | (40%) | (40%) | (40%) | (40%)   |              |
| Peptide | 18     | 12    | 10    | 10    | 10    | 10    | 10      |              |
| I       | (90%)  | (60%) | (50%) | (50%) | (50%) | (50%) | (50%)   | $p < 0.01$   |
| Peptide | 20     | 12    | 12    | 12    | 12    | 12    | 12      |              |
| II      | (100%) | (60%) | (60%) | (60%) | (60%) | (60%) | (60%)   | $p < 0.001$  |
| PmB     | 18     | 14    | 12    | 0     | 0     | 0     | 0       |              |
|         | (90%)  | (70%) | (60%) | (0)%  | (0)%  | (0)%  | (0)%    | n. s.        |

There were 20 mice per group. Mice surviving at each of the seven 24 hours observation periods are listed. The % survival appears in parenthesis. P expresses the level of statistical significance calculated by "t-Test" for each molecule compared to the treatment with saline, considering the total survival rate in each group.

Peptide I and Peptide II show safety and efficacy in comparison to PmB ($p <0.001$).

I claim:

1. A method for the removal of endotoxin from human and animal blood sera which comprises contacting said blood or sera with a peptide of which is a monomeric, linear polymeric, cyclic monomeric or cyclic polymeric peptide of the formula:

$$R_1\text{—}(A\text{—}B\text{—}C)_n\text{—}R \qquad (I)$$

wherein $R_1$ and R are independently H or an amino acid residue or a fatty acid residue; A is an amino acid residue selected from the group consisting of Lys and Arg; B is an amino acid selected from the group consisting of Phe, Tyr and Trp; C is an amino acid selected from the group consisting of Leu, Ile and Val; n is an integer of from 1–100, in an amount which is effective for the removal of endotoxin from said blood or sera.

2. A method for the detoxification of bacterial endotoxins which comprises treating the affected host with an amount of a peptide which is a monomeric, linear polymeric, cyclic monomeric or cyclic polymeric peptide of the formula:

$$R_1\text{—}(A\text{—}B\text{—}C)_n\text{—}R \qquad (I)$$

wherein $R_1$ and R are independently H or an amino acid residue or a fatty acid residue; A is an amino acid residue selected from the group consisting of Lys and Arg; B is an amino acid selected from the group consisting of Phe, Tyr and Trp; C is an amino acid selected from the group consisting of Leu Ile and Val; n is an integer of from 1–100 which is effective to detoxify any endotoxin which is in an affected host.

3. A method for the detoxification of a bacterial endotoxin which comprises contacting the bacterial endotoxin or a fluid containing the endotoxin with an amount of a peptide, which is effective for detoxification of said bacterial endotoxin, said peptide being a monomeric, linear polymeric, cyclic monomeric or cyclic polymeric peptide of the formula:

$$R_1-(A-B-C)_n-R \quad (I)$$

wherein $R_1$ and R are independently H or an amino acid residue or a fatty acid residue.; A is an amino acid residue selected from the group consisting of Lys and Arg; B is an amino acid selected from the group consisting of Phe, Tyr and Trp; C is an amino acid selected from the group consisting of Leu, Ile and Val; n is an integer of from 1–100.

4. A method for preventing contamination of a product with endotoxin, said method comprising adding to a product an amount of a peptide which is a monomeric, linear polymeric, cyclic monomeric or cyclic polymeric peptide of the formula:

$$R_1-(A-B-C)_n-R \quad (I)$$

wherein $R_1$ and R are independently H or an amino acid residue or a fatty acid residue; A is an amino acid residue selected from the group consisting of Lys and Arg; B is an amino acid selected from the group consisting of Phe, Tyr and Trp; C is an amino acid selected from the group consisting of Leu, Ile and Val; n is an integer of from 1–100 which is effective to neutralize any endotoxin which is subsequently elaborated by bacterial growth.

5. A method as defined in claim 2 wherein the peptide is of the formula:

Cys—Lys—Phe—Leu—Lys—Lys—Cys
S —— —— —— —— —— —— S   (SEQ ID NO: 1).

6. A method as defined in claim 2 wherein the peptide is of the formula:

Lys—Thr—Lys—Cys—Lys—Phe—Leu—Lys—Lys—Cys
                S —— —— —— —— —— —— S
(SEQ ID NO: 2).

7. A method as defined in, claim 2 wherein the peptide is of the formula:

Lys-Phe-Leu-Lys-Lys-Thr       (SEQ ID NO:3).

8. A method as defined in claim 2 wherein the peptide is of the formula:

Cys—Lys—Lys—Leu—Phe—Lys—Cys—Lys—Thr—Lys
S —— —— —— —— —— —— S   (SEQ ID NO: 4).

9. A method as defined in claim 2 wherein the peptide is of the formula:

Cys—Lys—Lys—Leu—Phe—Lys—Cys—Lys—Thr
S —— —— —— —— —— —— S   (SEQ ID NO: 5).

10. A method as defined in claim 2 wherein the peptide is of the formula:

Ile—Lys—Thr—Lys—Cys—Lys—Phe—Leu—Lys—Lys—Cys
                S —— —— —— —— —— —— S
(SEQ ID NO: 6).

11. A method as defined in claim 2 wherein the peptide is of the formula:

Ile—Lys—Thr—Lys—Lys—Phe—Leu—Lys—Lys—Thr
(SEQ ID NO:7).

12. A method as defined in claim 2 wherein the peptide is of the formula:

Ile—Lys—Phe—Leu—Lys—Phe—Leu—Lys—Phe—Leu—Lys
(SEQ ID NO:8).

13. A method as defined in claim 2 wherein the peptide is of the formula:

Lys—Phe—Leu—Lys—Phe—Leu—Lys       (SEQ ID NO:9).

14. A method as defined in claim 2 wherein the peptide is of the formula:

Arg-Tyr-Val-Arg-Tyr-Val-Arg-Tyr-Val       (SEQ ID NO:10).

* * * * *